US009987089B2

United States Patent
Chen et al.

(10) Patent No.: US 9,987,089 B2
(45) Date of Patent: Jun. 5, 2018

(54) DEVICE AND A METHOD FOR IMAGING-GUIDED PHOTOTHERMAL LASER THERAPY FOR CANCER TREATMENT

(71) Applicant: UNIVERSITY OF CENTRAL OKLAHOMA, Edmond, OK (US)

(72) Inventors: Wei R. Chen, Edmond, OK (US); Feifan Zhou, Edmond, OK (US); Zhifang Li, Fujian (CN); Hui Li, Fujian (CN)

(73) Assignee: University of Central Oklahoma, Edmond, OK (US)

( * ) Notice: Subject to any disclaimer, the term of this patent is extended or adjusted under 35 U.S.C. 154(b) by 209 days.

(21) Appl. No.: 14/797,430

(22) Filed: Jul. 13, 2015

(65) Prior Publication Data
US 2017/0014186 A1     Jan. 19, 2017

(51) Int. Cl.
    *A61B 18/20*     (2006.01)
    *A61B 18/22*     (2006.01)
    (Continued)

(52) U.S. Cl.
    CPC ............ *A61B 18/22* (2013.01); *A61B 5/0095* (2013.01); *A61B 5/4836* (2013.01);
    (Continued)

(58) Field of Classification Search
    CPC ..... A61B 18/22; A61B 5/0095; A61B 5/4836; A61B 2018/00702; A61B 2018/00761;
    (Continued)

(56) References Cited

U.S. PATENT DOCUMENTS

| 4,936,308 A | 6/1990 | Fukukita et al. |
| 8,328,721 B2 | 12/2012 | Savery et al. |
| (Continued) | | |

FOREIGN PATENT DOCUMENTS

| CN | 103919607 | * 7/2014 | ............ A61B 18/22 |
| EP | 2559375 | 2/2013 | |
| (Continued) | | | |

OTHER PUBLICATIONS

Shah et al., Photoacoustic Imaging and Temperature Measurement for Photothermal Cancer Therapy, 2008, J. Biomed Opt., 13(3).*
(Continued)

*Primary Examiner* — Aaron Roane
(74) *Attorney, Agent, or Firm* — Berenato & White, LLC (57) ABSTRACT

This invention relates to a device and a method for monitoring and optimizing photothermal therapy, using a high-power continuous-wave laser beam and a pulsed laser beam, both transmitted through a single soft, multi-mode optical fiber with a diffuse active tip, to interstitially irradiate the target tissue at the same time. The continuous-wave laser light induces photothermal effect and increases tissue temperature and the pulsed laser light produces a photoacoustic signal. The photoacoustic signal intensity is used to monitor the temperature changes in the target tissue and to guide the irradiation of the high-power laser to optimize the photothermal effect by adjusting the light intensity and irradiation time.

8 Claims, 8 Drawing Sheets

(51) Int. Cl.
*A61B 5/00* (2006.01)
*A61B 18/00* (2006.01)

(52) U.S. Cl.
CPC ............. *A61B 2018/00702* (2013.01); *A61B 2018/00761* (2013.01); *A61B 2018/00791* (2013.01); *A61B 2018/2005* (2013.01); *A61B 2018/2025* (2013.01); *A61B 2018/2261* (2013.01)

(58) Field of Classification Search
CPC .. A61B 2018/00791; A61B 2018/2005; A61B 2018/2025; A61B 2018/2261
USPC .......................................................... 606/1
See application file for complete search history.

(56) References Cited

U.S. PATENT DOCUMENTS

| | | | |
|---|---|---|---|
| 8,337,433 | B2 | 12/2012 | Cerwin et al. |
| 8,343,050 | B2 | 1/2013 | Fan et al. |
| 8,864,669 | B2 | 10/2014 | Behar |
| 8,870,772 | B2 | 10/2014 | Behar |
| 8,882,672 | B2 | 11/2014 | Behar |
| 8,971,998 | B2 | 3/2015 | Messano et al. |
| 2003/0167002 | A1 | 9/2003 | Nager et al. |
| 2004/0034304 | A1 | 2/2004 | Sumi |
| 2006/0241484 | A1 | 10/2006 | Horiike et al. |
| 2007/0106157 | A1 | 5/2007 | Kaczkowski et al. |
| 2008/0081995 | A1 | 4/2008 | Kim et al. |
| 2009/0105588 | A1* | 4/2009 | Emelianov ............ A61B 5/4869 600/438 |
| 2009/0234228 | A1 | 9/2009 | Pintel et al. |
| 2010/0043557 | A1 | 2/2010 | Savery et al. |
| 2011/0046487 | A1 | 2/2011 | Shin et al. |
| 2011/0270071 | A1 | 11/2011 | Furukawa |
| 2011/0306881 | A1 | 12/2011 | Liu et al. |
| 2012/0125107 | A1* | 5/2012 | Emelianov ............ A61B 5/0095 73/579 |
| 2012/0157838 | A1 | 6/2012 | Adanny et al. |
| 2013/0006088 | A1 | 1/2013 | Miyasato |
| 2013/0035592 | A1 | 2/2013 | Messano, Jr. et al. |
| 2013/0096422 | A1 | 4/2013 | Boctor et al. |
| 2013/0116562 | A1 | 5/2013 | Kong et al. |
| 2013/0281877 | A1 | 10/2013 | Hsu et al. |

FOREIGN PATENT DOCUMENTS

| | | |
|---|---|---|
| WO | WO2011042894 | 4/2011 |
| WO | WO2011080712 | 7/2011 |
| WO | WO2011080713 | 7/2011 |
| WO | WO2011096551 | 8/2011 |

OTHER PUBLICATIONS

Hirsch, L.R.; Stafford, R.J.; Bankson, J.A.; Sershen, S.R.; Rivera, B.; Price, R.E.; Hazle, J.D.; Halas, N.J.; West, J.L., Nanoshell-mediated near-infrared thermal therapy of tumors under magnetic resonance guidance. PNAS 2003, 100, 13549-13554.

Li, X.; Naylor, M.F; Nordquist, R.E.; Teague, T.K.; Howard, C.A.; Murray, C.; Chen, W.R., Clinical effects of in situ photoimmunotherapy for late-stage melanoma patients: A preliminary study. Cancer Biol. Ther. 2010, 1081-1087.

Zhang, H.G.; Mehta, K.; Cohen, P.; Guha, C., Hyperthermia on immune regulation: A temperature's story. Cancer Lett. 2008, 271, 191-204.

Li, X.; Gu, Y.; Du, N.; Hode, T.; Nordquist, R.E.; Wolf, R.F.; Howard, E.; Lunn, J.A.; Adalsteinsson, O.; Chen, W.R., Laser immunotherapy: Concept, possible mechanism, clinical applications, and recent experimental results. IEEE J. Sel. Top. Quantum Electron. 2012, 18, 1434-1438.

Mital, M.; Scott, E.P., Thermal detection of embedded tumors using infrared imaging. J. Biomech. Eng. 2007, 129, 33-39.

Gescheit, I.M.; Dayan, A.; Ben-David, M.; Gannot, I., Minimal-invasive thermal imaging of a malignant tumor: A simple model and algorithm. Med. Phys. 2010, 37, 211-216.

Varghese, T.; Zagzebski, J.A.; Chen, Q.; Techavipoo, U.; Frank, G.; Johnson, C.; Wright, A.; Lee, F.T., Ultrasound monitoring of temperature change during radofrequency ablation: Preliminary in vivo results. Ultrasound Med. Biol. 2002, 28, 321-329.

Lereu, A.L.; Farahi, R.H.; Tetard, L.; Enoch, S.; Thundat, T.; Passian, V., Plasmon assisted thermal modulation in nanoparticles. Opt. Express 2013, 21, 12145-12158.

Li, Z.; Li, H.; Chen, H.; Xie, W., In vivo determination of acute myocardial ischemia based on photoacoustic imaging with a focused transducer. J. Biomed. Opt. 2011, 16, 076011-1-6.

Lutzweiler, C.; Razansky, D., Optoacoustic imaging and tomography: Reconstruction approaches and outstanding challenges in image performance and quantification. Sensors 2013, 13, 7345-7384.

Ritz, J.P.; Roggan, A.; Isbert, C.; Muller, G.; Buhr, H.J.; Germer, C.T., Optical properties of native and coagulated porcine liver tissue between 400 and 2400 nm. Lasers Surg. Med. 2001, 29, 205-212.

Mohammed, Y.; Verhey, J.F., A finite element method model to simulate laser interstitial thermotherapy in anatomical inhomogeneous regions. Biomed. Eng. Online 2005, 4, 2, 1-16.

Farahi, R.H.; Passian, A.; Tetard, L.; Thundat, T., Pump-probe photothermal spectroscopy using quantum cascade lasers. J. Phys. D Appl. Phys. 2012, 45, 125101, pp. 1-7.

Zhifang Li, Haiyu Chen, Feifan Zhou, Hui Li and Wei R. Chen., Interstitial Photoacoustic Sensor for the Measurement of Tissue Temperature during Interstitial Laser Phototherapy. Sensors 2015, 15(3), 5583-5593; doi:10.3390/s150305583.

Chen, W.R.; Adams, R.L.; Higgins, A.K.; Bartels, K.E.; Nordquist, R.E., Photothermal effects on murine mammary tumors using indocyanine green and an 808-nm diode laser: An in vivo efficacy study. Cancer Lett. 1996, 98, 169-173.

Chen, W R.; Zhu, W-G.; Dynlacht, J.R.; Liu, H.; Nordquist, R.E., Long-term tumor resistance induced by laser photo-immunotherapy. Int. J. Cancer 1999, 81, 808-812.

Chen, W.R.; Liu, H.; Nordquist, J.A.; Nordquist, R.E., Tumor cell damage and leukocyte infiltration after laser immunotherapy treatment. Lasers Med. Sci. 2000, 15, 43-48.

Chen, W.R.; Singhal, A.K.; Liu, H.; Nordquist, R.E, Antitimor immunity induced by laser immunotherapy and its adoptive transfer. Cancer Res. 2001, 61, 459-461.

Chen, W.R.; Liu, H.; Ritchey, J.W.; Bartels, K.E.; Lucroy, M.D.; Nordquist, R.E., Effect of different components of laser immunotherapy in treatment of metastatic tumors in rats. Cancer Res. 2002, 62, 4295-4299.

Chen, W.R.; Jeong, S.W.; Lucroy, M.D.; Wolf, R.F.; Howard, E.W.; Liu, H.; Nordquist, R.E., Induced antitumor immunity against DMBA-4 metastatic mammary tumors in rats using laser immunotherapy. Int. J. Cancer 2003, 107, 1053-1057.

Li, X.; Ferrel, G.L.; Guerra, M.C.; Hode, T.; Lunn, J.A.; Adalsteinsson, O.; Nordquist, R.E.; Liu, H.; Chen, W.R., Preliminary safety and efficacy results of laser immunotherapy for the treatment of metastatic breast cancer patients. Photochem. Photobiol. Sci. 2011, 10, 817-821.

Oh, T.I.; Kim, H.J.; Jeong, W.C.; Chauhan, M.; Kwon, O.I.; Woo, E.J., Detection of temperature distribution via recovering electrical conductivity in MREIT. Phys. Med. Biol. 2013, 58, 2697-2711.

Pramanik, M.; Wang, L.V., Thermoacoustic and photoacoustic sensing of temperature. J. Biomed. Opt. 2009, 14, 054024-1-7.

Le, K.; Li, X.; Figueroa, D.; Towner, R.A.; Garteiser, P.; Saunders, D.; Smith, N.; Liu, H.; Hode, T.; Nordquist, R.E.; et al., Assessment of thermal effects of interstitial laser phototherapy on mammary tumors using proton resonance frequency method. J. Biomed. Opt. 2011, 16, 128001-1-128001-10.

Chen, Y.; Gnyawali, S.C.; Wu, F.; Liu, H.; Tesiram, Y.A.; Abbott, A.; Towner, R.A.; Chen, W.R., Magnetic resonance imaging guidance for laser photothermal therapy. J. Biomed. Opt. 2008, 13, 044033-1-8.

(56) References Cited

OTHER PUBLICATIONS

Complete English Language Translation of CN103919607A, Li et al., Published Jul. 16, 2014.

* cited by examiner

DEVICE AND A METHOD FOR IMAGING-GUIDED PHOTOTHERMAL LASER THERAPY FOR CANCER TREATMENT

STATEMENT AS TO RIGHTS TO INVENTIONS MADE UNDER FEDERALLY SPONSORED RESEARCH OR DEVELOPMENT

This invention was made with government support under R21 EB0155091 awarded by the United States National Institutes of Health. The government has certain rights in the invention.

This invention was sponsored in part by the National Natural Science Foundation of China Grant Number (61178089/81201124), the Natural Science Foundation of Fujian Province (2012J05137), and by the Chinese Science Foundation of the National Health and Family Planning Commission (WKJ-FJ-22).

CROSS REFERENCES TO RELATED APPLICATIONS

This application incorporates herein by reference in its entirety Chinese Patent Application No. CN201310663899.0 filed on Dec. 11, 2013 in the name of Zhifang Li, Hui Li, and Wei R. Chen, published Jul. 16, 2014.

FIELD OF THE INVENTION

The present invention relates to photothermal therapy in cancer treatment. More particularly, the present invention relates to photothermal therapy using a high-power continuous-wave laser beam to induce photothermal effect and increase target tumor tissue temperature, and a pulsed laser beam to induce photoacoustic signals for monitoring the photothermal effect.

BACKGROUND OF THE INVENTION

Laser photothermal effect is a successful approach to tumor destruction since tumor tissue is more sensitive to temperature increases than normal tissue. In the past selective photothermal therapy using an in situ light-absorbing agent or nanoparticles has been developed. While photothermal interaction leads to acute, large-scale and controllable tumor destruction, its long-term effects are rather limited, particularly when treating metastatic cancers. However, laser-tissue thermal interaction can be used in combination with immunotherapy, as thermally destroyed tumor cells could serve as sources of tumor antigens, priming the host immune system. Laser immunotherapy (LIT) was developed as a synergistic approach to treat cancer systemically, through both local laser irradiation and immunological stimulation. LIT has shown great potential in treating late-stage, metastatic cancers, both in pre-clinical studies and in preliminary clinical trials. Interstitial laser immunotherapy (ILIT), using a fiber with a cylindrical active diffuse lens, can be an attractive alternative approach to overcome the challenges of non-invasive selective photothermal therapy, particularly when facing deep-seated tumors and highly pigmented skins.

The immunomodulatory effects of thermal interaction have been categorized in three different temperature ranges: fever range (39-40° C.), heat shock range (41-43° C.) and cytotoxic range (>43° C.) [14]. In the first two ranges, the thermal effect modifies both tumor cells and immune cells to stimulate host tumor-specific immune response. In the third range, high temperatures can lead to direct destruction of tumor cells, releasing a large load of tumor antigens; these are taken up by antigen-presenting cells, particularly dendritic cells, and delivered to lymph nodes where they induce an antitumor immune response. The optimal outcome of photothermal tissue interaction, therefore, is to destroy as many target tumor cells as possible, while preserving tumor proteins to be recognized by the host immune system. Laser immunotherapy can achieve a maximum temperature of up to 60 to 70° C., well within the cytotoxic range. At these temperatures, cell death occurs through coagulation necrosis. The aim of laser immunotherapy is to control the target tissue temperature at an optimal level, which will be determined under different conditions, for the treatment of tumors.

Since temperature plays an important role in laser phototherapy, accurate temperature measurement and control are crucial. Current non-invasive methods in tissue temperature measurement include infrared thermography, ultrasound imaging, and magnetic resonance thermometry (MRT). Infrared thermography can provide sensitive, real-time detection; however, this can measure surface temperature only. Ultrasound can reach deep tissues, but it has relatively low sensitivity and accuracy. Temperature measurements, based on water proton resonance frequency (PRF) in MRT, exploit the temperature dependency of the water proton's chemical shift to determine tissue temperature of each voxel; and this has been used for interstitial laser therapy. MRT provides non-invasive three-dimensional temperature distribution with high sensitivity. However, MRT has relatively low temporal resolution, and its cost and complexity severely limit its practical applications.

Previous reports have shown that photoacoustic (PA) imaging can be used for temperature measurements in tissue. PA signal amplitude shows a linear correlation with temperatures in the range of 10 to 55° C., just below the desired threshold temperature of biological responses. It is therefore an objective of the present invention to use PA imaging in a method and apparatus to provide tissue temperature monitoring and laser phototherapy control to optimize thermal effects and for modulating immune responses. It is a further objective of the present invention to provide an interstitial PA sensor for the real-time measurement of tissue temperature, as well as other tissue properties, during interstitial laser phototherapy.

SUMMARY OF THE INVENTION

The method and apparatus of the present invention provides an interstitial PA sensor developed for the real-time measurement of tissue temperature during interstitial laser phototherapy. This unique sensor converges a continuous-wave laser light and a pulsed laser light through a fiber coupler to a cylindrical diffuse active lens, and delivers the lights to the same target area at the same time. The two laser lights are used for therapeutic photothermal irradiation and photoacoustic temperature measurement, respectively. Using this sensor, the maximum temperature increase can be measured in target tissue which surrounds a cylindrical active fiber tip. With the use of a bioheat equation, tissue temperature can be determined in the region of interest. The method and apparatus of the present invention provides a unique sensor for guidance and control of laser phototherapy in cancer treatment.

In a broad aspect, the apparatus and method of the present invention provides a capability for monitoring and optimizing photothermal tissue effect, coupling a high-power continuous-wave laser beam and a pulsed laser beam through a single soft, multi-mode optical fiber with a diffuse active tip, to interstitially irradiate simultaneously the target tissue.

In another aspect, the apparatus and method of the present invention induces photothermal effect and increases target tissue temperature using continuous-wave laser light and produces a photoacoustic signal using the pulsed laser light.

In another aspect, the temperature changes in the target tissue are monitored using the photoacoustic signal intensity.

In another aspect, the irradiation of the high-power laser during phototherapy is guided using the temperature profiles of the target tissue.

In another aspect, the photothermal effect is optimized by adjusting the intensity and irradiation time of the high-power laser.

In another broad aspect, the method of the present invention employs an apparatus comprising a continuous-wave laser, a pulse laser, an optical fiber coupling component, a computer component, an acoustic coupling component, a scanning component connected to computer, a sample stabilizing component, an data acquisition card connected to a ultrasound energy exchanger, and to a computer network.

In another aspect, the method of the present invention provides a continuous-wave laser beam and a pulse laser beam to irradiate the same target tissue through an active tip of a diffuse fiber.

In another aspect, the method and apparatus of the present invention provide a continuous-wave laser beam and a pulse laser beam delivered to a target tissue at the same time through an optical fiber coupling component to a single fiber with a diffuse active tip.

BRIEF DESCRIPTION OF THE DRAWINGS

FIG. 4 is a non-limiting diagram showing temperature measurements taken during experimental testing, where

FIG. 7 is a non-limiting diagram showing a two-dimensional temperature distribution in a target tissue as measured during an experimental testing under different irradiation conditions, where temperature distribution with a maximum temperature of 41° C. is shown in FIG. 7*a*; and temperature distribution with a maximum temperature of 55° C. is shown in FIG. 7*b*.

DETAILED DESCRIPTION OF PREFERRED EMBODIMENTS OF THE INVENTION

Figure 1:
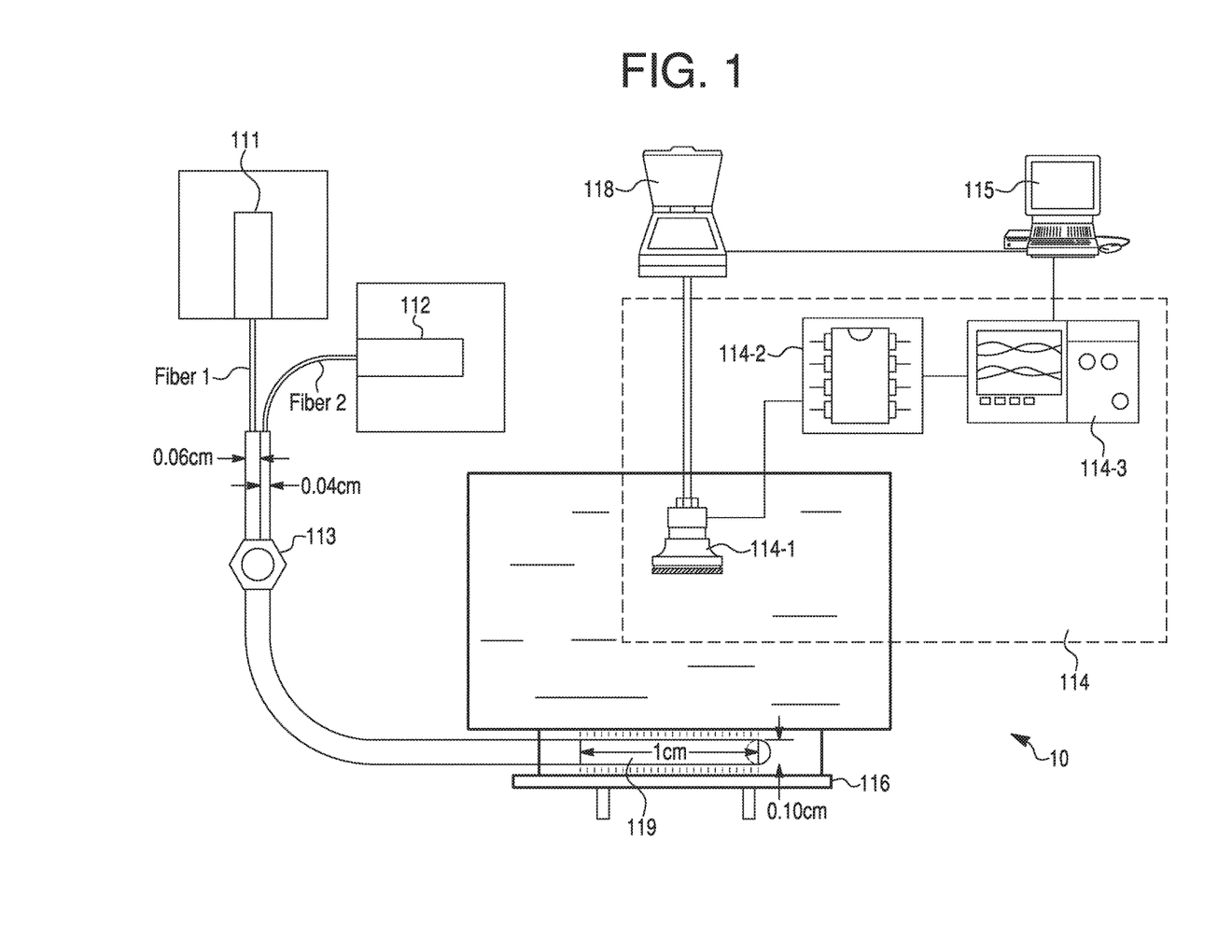
FIG. 1 is a non-limiting diagram showing the apparatus for imaging-guided photothermal laser therapy for cancer treatment.

In brief: FIG. 1 is a non-limiting diagram showing the apparatus of the present invention enabling imaging-guided photothermal laser therapy for cancer treatment using a high-power laser beam for interstitial thermal effect and a pulse laser for photoacoustic effect converging to the target tissue through a fiber coupler. The apparatus comprises at least: a pulse laser; a continuous-wave laser; an optical fiber coupler component; a photoacoustic signal acquisition component including a water-submerging focusing ultrasound energy exchanger, signal amplifier, and oscilloscope; a computer and processing unit; a sample-stabilizing platform; a photoacoustic coupling component; and a scanning component.

Figure 2:
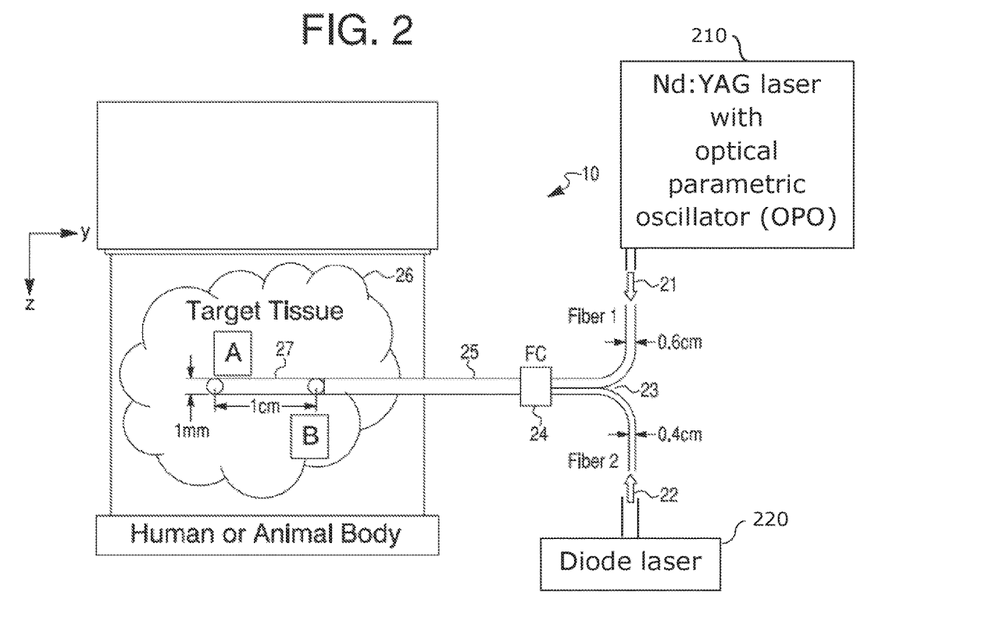
FIG. 2 is a non-limiting diagram showing the light beam from a laser delivered to biological target tissue.

FIG. 2 is a non-limiting diagram showing the light beam from a laser with an optical parametric oscillator (OPO) delivered to biological target tissue, human or animal. The light beam from OPO is delivered to the biological target tissue by optical fiber 1. A diode laser is used to produce through optical fiber 2 the photothermal effect.

Figure 3:
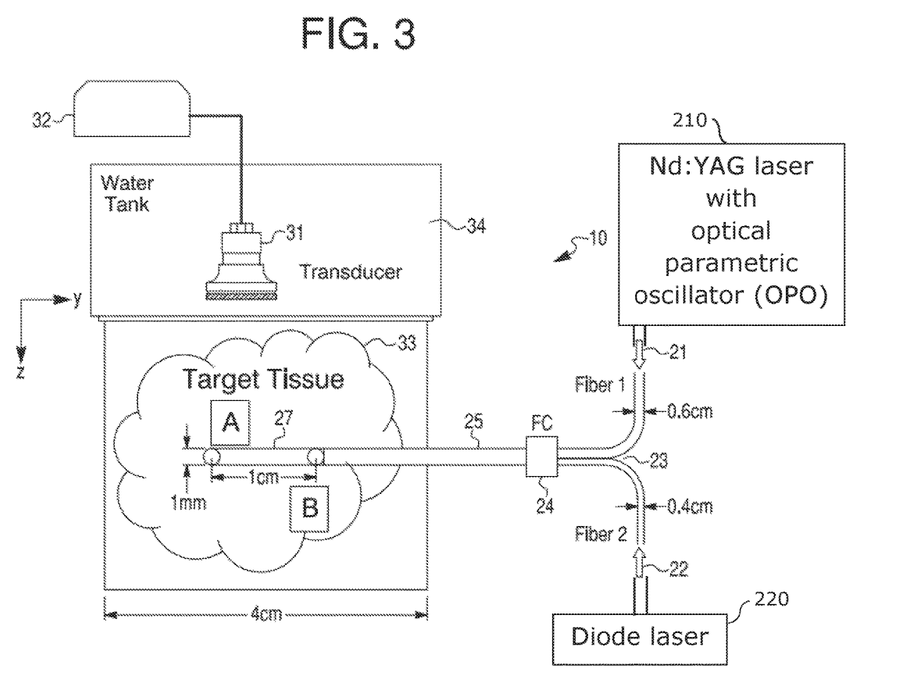
FIG. 3 is a non-limiting diagram showing a laboratory test setup. A fiber with an active tip may be placed in the center of a target tissue. Both pulse laser light and continuous-wave laser light may be directed through two different fibers (1 and 2) into the same active tip (1-cm length and 1-mm diameter) in the target tissue through a fiber coupler.

FIG. 3 is a non-limiting diagram showing a fiber with a 1.0-cm active tip placed in the center of a target tissue. Both pulse laser light and continuous-wave laser light may be directed through two different fibers (1 and 2) into the same active tip (1-cm length and 1-mm diameter) in the target tissue through a fiber coupler. The photoacoustic signals at position A may be detected for temperature determination. A thermocouple needle probe may be placed at position B, symmetric to position A, to calibrate the PA measurement of tissue temperature. For purpose of laboratory testing, a water tank may be placed on top of the target tissue to enhance the acoustics coupling.

Figure 4A:
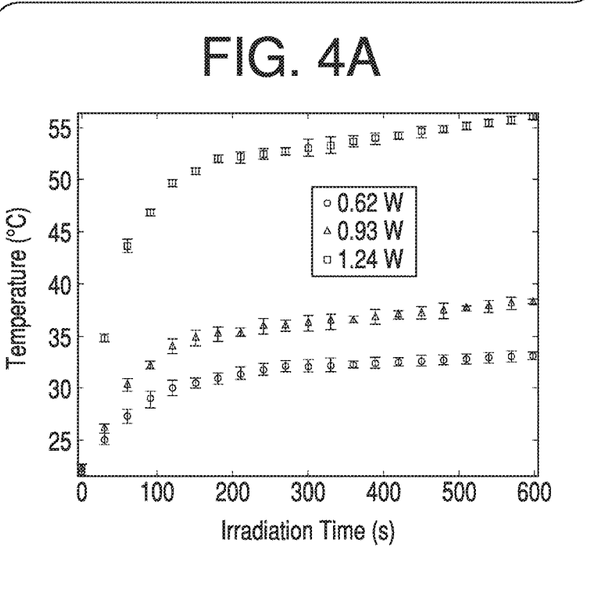
FIG. 4*a* shows temperature measured by a thermocouple and FIG. 4*b* shows the photoacoustic amplitude measured by a sensor.
Figure 4B:
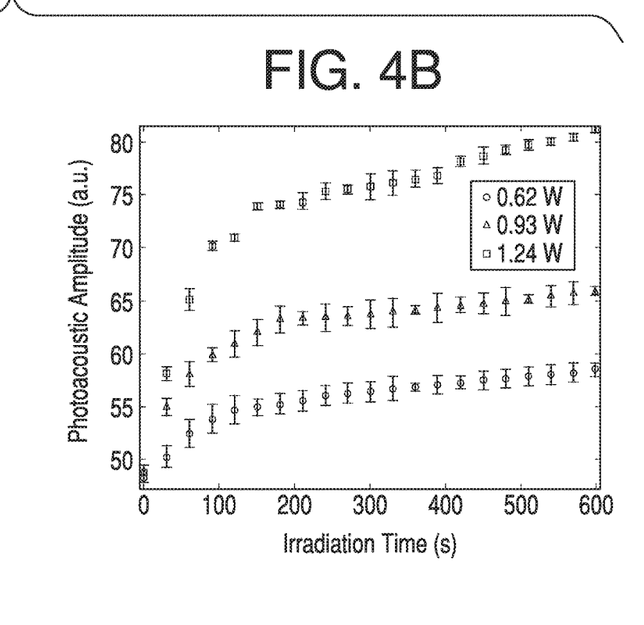

FIG. 4 is a non-limiting diagram showing temperature measurements taken during experimental testing. Temperature T shown in FIG. 4*a* was measured by thermocouple (a) and the photoacoustic amplitude shown in FIG. 4*b* was measured by the sensor (b), at positions B and A, respectively (see FIG. 2), under interstitial laser irradiation of different powers.

Figure 5:
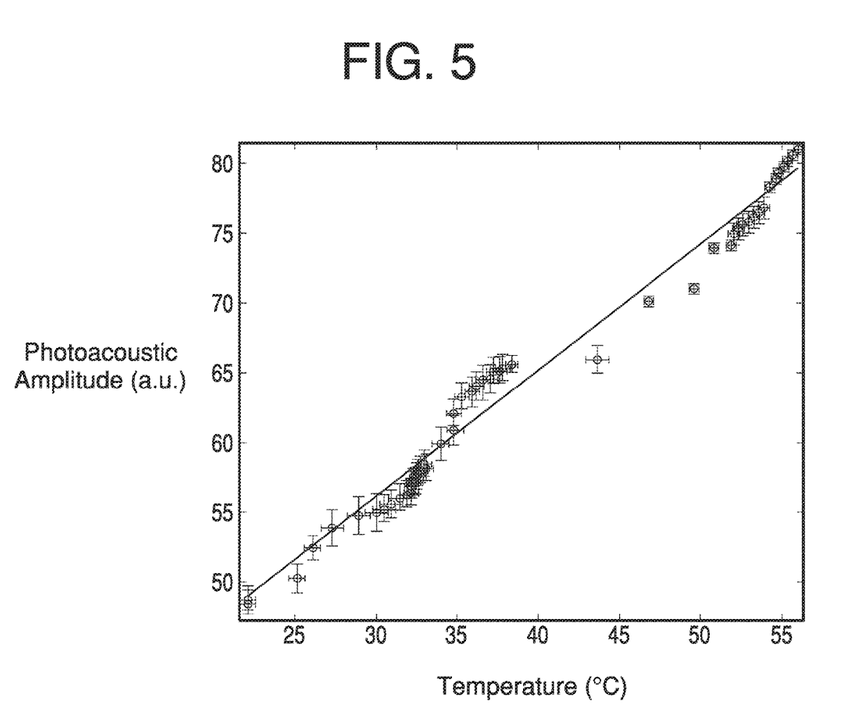
FIG. 5 is a non-limiting diagram showing in experimental testing the relationship between photoacoustic signal at position A and temperature at position B (see FIG. 2).

FIG. 5 is a non-limiting diagram showing in experimental testing the relationship between photoacoustic signal at position A and temperature at position B (see FIG. 2). The straight line is a regression curve at 95% confidence ($r^2 > 0.94$ and p-value <0.01).

Figure 6:
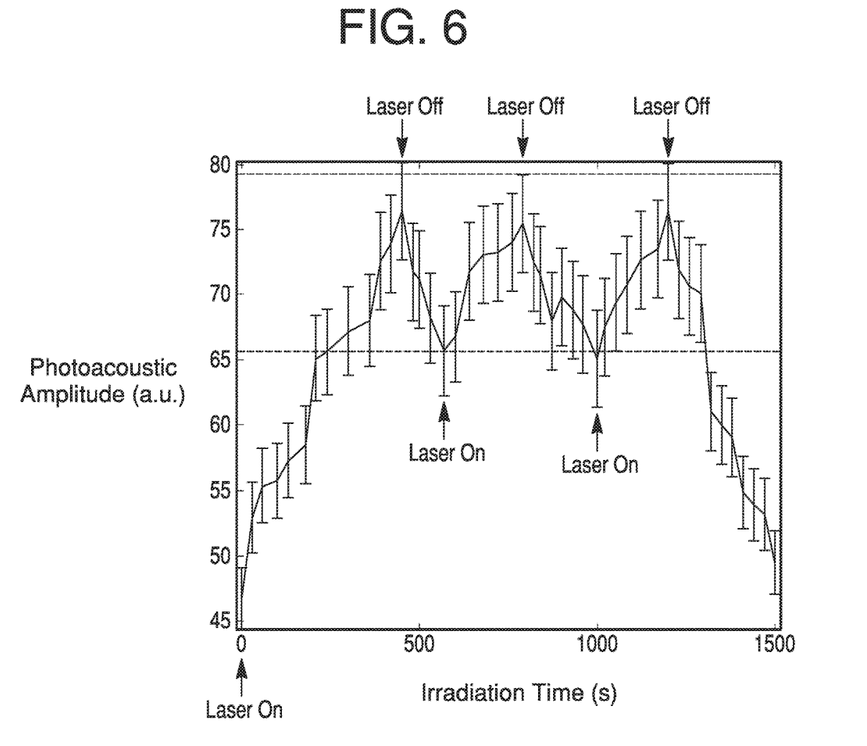
FIG. 6 is a non-limiting diagram showing photoacoustic amplitude versus irradiation time measured during an experimental testing with a control of laser parameters.

FIG. 6 is a non-limiting diagram showing photoacoustic amplitude versus irradiation time measured during experimental testing. The laser power for thermal irradiation was 1.24 W. The two dotted lines represent the PA amplitudes for the corresponding temperatures at 41 and 55° C., respectively, based on the linear relationship between PA signals and temperature (FIG. 5).

Figure 7A:
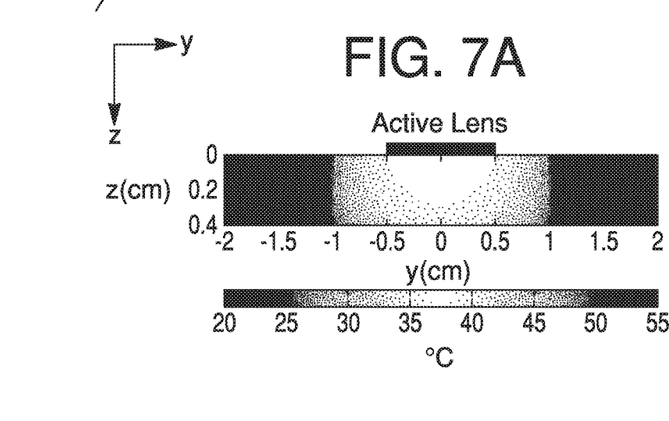
Figure 7B:
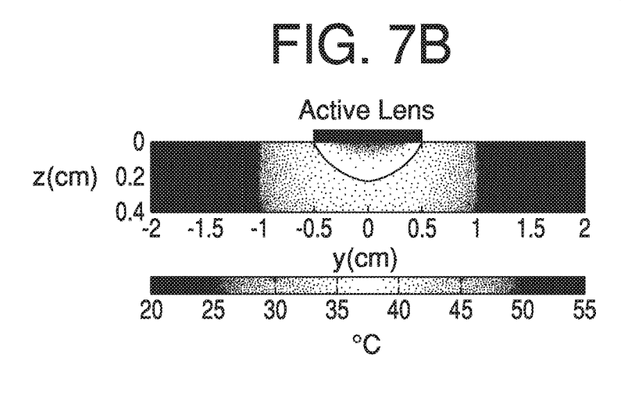

FIG. 7 is a non-limiting diagram showing a two-dimensional temperature distribution in a target tissue as measured during experimental testing. The active diffusion tip is along the y direction, while the z direction is perpendicular to the active tip. Temperature distribution with a maximum temperature of 41° C. is shown in FIG. 7*a*; Temperature distribution with a maximum temperature of 55° C. with the black curve denoting a temperature of 41° C. is shown in FIG. 7*b*.

Figure 8:
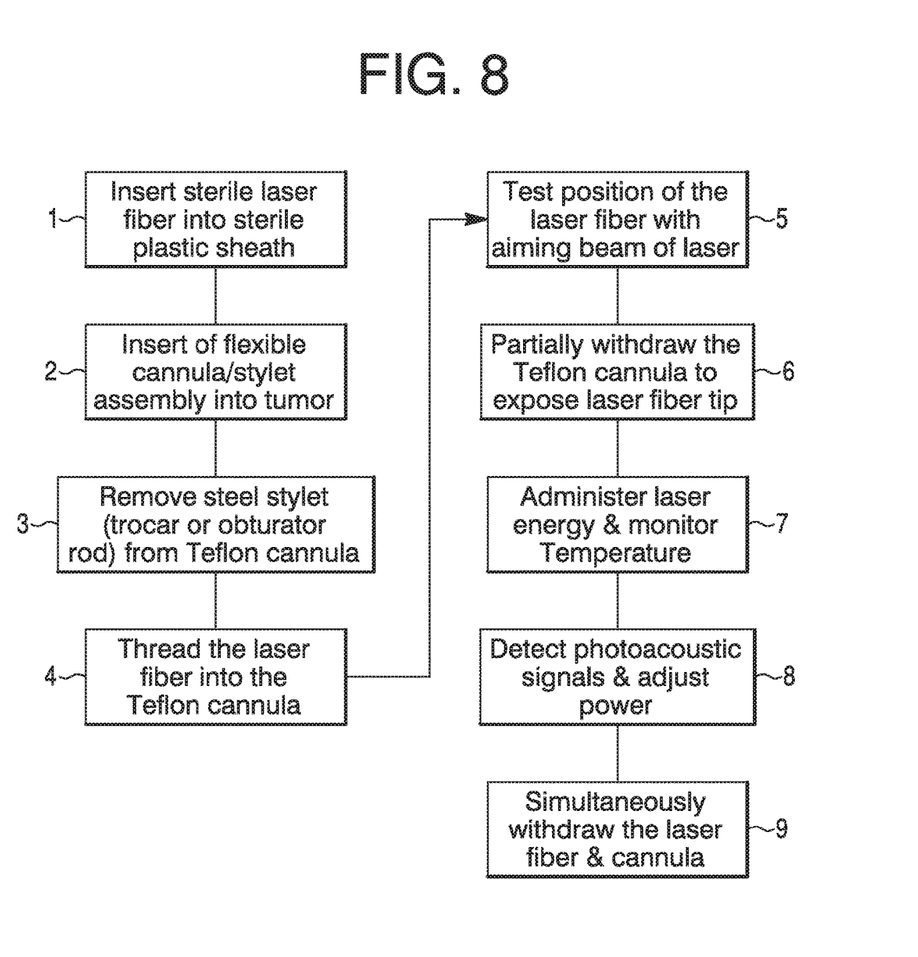
FIG. 8 is a non-limiting diagram showing use of present invention when laser photothermal therapy is performed on a target tumor.

FIG. 8 is a non-limiting diagram showing method of using present invention when performing interstitial laser photothermal therapy.

In detail: Referring now to FIG. 1, a non-limiting schematic illustration of one embodiment of the present invention 10 shows a pulse laser 1 (111); a continuous-wave laser 2 (112); an optical fiber coupler component 3 (113); a photoacoustic signal acquisition component 4 comprising a water-submerging focusing ultrasound energy exchanger (114-1), signal amplifier (114-2), and oscilloscope (114-3); a computer and processing unit (115); a sample-stabilizing platform (116);

a photoacoustic coupling component; a scanning component (118), and a cannula/stylet needle assembly (119). The pulsed laser 1 (111) may be used for photoacoustic temperature measurement. The continuous-wave laser 2 may be used for photothermal irradiation. The optical fiber coupler component (113) may be used to deliver laser light received through Fibers 1 and 2 to target tissue. The photoacoustic signal acquisition component (114) comprises a water-submerging focusing ultrasound energy exchanger (114-1), signal amplifier (114-2), and oscilloscope (114-3), for detection of photoacoustic signals generated in target tissue. The computer and processing unit (115) may be used to govern the operating state of the pulse laser and the continuous-wave laser to control the temperature in the optimal range at strategic positions in target tissue. The sample-stabilizing platform (116) may be used during laboratory experimentation to hold sample tissue. The photoacoustic coupling component (113) may be used to converge light beams from two fibers. The scanning component (118, 116, and 114-1) may be used for 2-dimensional scanning.

A Nd:YAG laser with OPO oscillator may be used for photoacoustic wave generation with a wavelength of 810 nm, a repetition frequency of 10 Hz, a pulse width of 6 ns, and output energy of ~6 mJ. The light beam from OPO may be divided into two beams using a splitter mirror. One beam may be received by a photodiode and displayed on an oscilloscope for calibration, while the other may be delivered to target tissue.

Referring now to FIG. 2, a non-limiting schematic illustration of one embodiment of the present invention 10 shows the light beam 21 from OPO 210 delivered to biological target tissue by Fiber 1 using a core diameter of 600 μm to generate the PA signal. A diode laser 220 having a wavelength 810 nm, power range 1~30 W, may be used to deliver a light beam 22 through Fiber 2 with a core diameter of 400 μm for photothermal effect. Different laser powers, e.g., 0.63, 0.93, and 1.24 W, may be selected for thermal irradiation. The two optical fibers 23 may be placed in parallel; light beams 21 and 22 from two fibers 23 can then be converged through a coupler 24 to the same fiber 25 (core diameter of 1000 μm) with the diffuse active tip.

The depth-resolved photoacoustic signals from the target tissue 26 may be collected by a focused ultrasound transducer [FIG. 3-31], with a center frequency at approximately 3.5 MHz. The signals may then be transferred to an ultrasonic receiver [FIG. 3-32] for amplitude filtering and amplification. Finally, the signals may be displayed on a digital oscilloscope [FIG. 1-114-3]. In order to improve the signal-to-noise ratio, the signals on the digital oscilloscope [FIG. 1-114-3] can be averaged 6 to 10 times and then saved for follow-up data processing. The axial and lateral spatial resolutions of the PA imaging may be set at approximately 0.3 and 2 mm, respectively. Target tissue may be located within the human body or the body of an animal.

Referring now to FIG. 3, a fiber 25 with an active tip 27 sized at approximately 1.0-cm may be placed in the center of the target tissue 26. Both pulse laser light and continuous-wave laser light may then be directed through two different fibers (1 and 2) into the same active tip 27 (e.g., 1-cm length and 1-mm diameter) in the target tissue 26 through a fiber coupler 24. The photoacoustic signals at position A may be detected for temperature determination. A thermocouple needle probe may be placed at position B, symmetric to position A, to calibrate the PA measurement of tissue temperature.

Theoretical Foundation of PA Measurement of Temperature

The method and apparatus of the present invention was developed through a series of testing regimens that validate theoretical constructs. The imaging method based on the photoacoustic effect uses a short pulse laser to illuminate absorbers in tissue to generate acoustic waves. The measured PA pressure that satisfies the temporal stress confinement is given by:

$$P(z)=\Gamma\mu_a F(z,\mu_a,\mu_s,g) \tag{1}$$

where $\Gamma=\beta c^2/C_p$ is Grüneisen parameter, $\beta$ is the expansion coefficient, c is the speed of sound, $C_p$ is the specific heat, $F(z, \mu_a, \mu_s, g)$ is the local optical fluence, z is the one-dimensional incident depth, $\mu_a$ is the absorption coefficient, $\mu_s$ is the scattering coefficient, and g is the anisotropic factor. The Grüneisen parameter $\Gamma$ is linearly proportional to temperature T in the range of 10 to 55° C. for soft tissues, $$\Gamma=A+BT \tag{2}$$

where A and B are constants. Thus, Equation (1) can be further written as:

$$P(z)=(A+BT)\mu_a F(z,\mu_a,\mu_s,g) \tag{3}$$

During interstitial laser phototherapy, the temperature T changes as a function of both irradiation time and laser power. The light emitted from an interstitial fiber was modeled as an isotropically diffusive regime, and the local optical fluence can be expressed as $F(z, \mu_a, \mu_s, g) \propto \exp(-\mu_{eff} z)$, where $\mu_{eff}=\sqrt{3\mu_a[\mu_a+\mu_s(1-g)]}$ is the effective attenuation coefficient. Based on the values of the absorption coefficient, scattering coefficient, and anisotropic factor of liver tissue (0.73, 0.55 and 0.93 cm$^{-1}$, respectively) at the wavelength of 810 nm, we found that $\mu_{eff}=3.2$ cm$^{-1}$. The detected superficial PA signal from position A (0.2 mm from the surface of the active tip) was approximated as the superposition of the PA signal P(z) from a depth of 0.05 to 0.35 mm, since the axial spatial resolution of PA imaging was 0.3 mm. Tissue temperature T increases with interstitial irradiation using cylindrical diffusion light. The light diffusion approximation is given by:

$$-D\nabla^2\varphi(r)+\mu_a\varphi(r)=s(r) \tag{4}$$

where $\varphi$ is the light power density (W·cm$^{-2}$), D is the diffusion coefficient (cm$^{-1}$), $\mu_{eff}=(\mu_a/D)^{1/2}$, and s is the source term (W·cm$^{-3}$). The solution to Equation (4) for an isotropic point light source with power $P_0$ within an infinite homogeneous medium can be expressed as:

$$\varphi(r)=\frac{P_0\exp(-\mu_{eff}r)}{4\pi Dr} \tag{5}$$

The deposited light power S can then be determined as $S=\mu_a\varphi(r)$. The Pennes bioheat equation can be used to describe the steady-state temperature fields of tissue irradiated by laser light using an interstitial diffuse fiber; this is modeled as multiple isotropically radiating point sources distributed along the fiber tip with an interval of 1 mm:

$$\rho \cdot c \cdot \frac{\partial T(r, t)}{\partial t} = \nabla \cdot [k \cdot \nabla T(r, t)] + \sum S(r, t) \quad (6)$$

where ρ is the density of tissue [kg·cm$^{-3}$], c is specific heat of tissue [J·Kg$^{-1}$·°C.$^{-1}$], k is the thermal conductivity of tissue [W·cm$^{-1}$·°C.$^{-1}$], r is the position vector [cm], t is the time [s], and S is the deposited light power [W·cm$^{-3}$]. Using Equation (4), tissue temperature can be determined using a simulation program, COMSOL MULTIPHYSICS 5.0. The optical and thermal properties used in Equations (4) to (6) for the simulation are given in Tables 1 and 2 for liver tissue.

TABLE 1

Optical properties variables for liver tissue.

| Anisotropic Factor (g) | Scattering Coefficient ($\mu_s$) | Absorption Coefficient ($\mu_a$) |
|---|---|---|
| 0.93 | 5.6 mm$^{-1}$ | 0.73 mm$^{-1}$ |

TABLE 2

Thermal and physiological properties of liver tissue [31].

| ρ (g/cm$^3$) | c (J·g$^{-1}$·°C.$^{-1}$) | k (W·cm$^{-1}$·°C.$^{-1}$) |
|---|---|---|
| 1.05 | 3.59 | 0.00566 |

Experimental Setup

Referring now to FIG. 3, sample tissue 33 was used in an experiment to test and validate the efficacy of the present invention FIG. 1-10. The size of the sample tissue 33 used was 4 cm×4 cm×1 cm. The pig liver tissue 33 was placed at room temperature (22° C.) prior to the experiment. An optical fiber 25 with a 1.0-cm cylindrical diffuse active tip 27 was placed in the center of the tissue 33, as shown in FIG. 3. Two laser beams 21 and 22 were merged through a fiber coupler 24 with a core diameter of 1000 μm. The PA signal at position A (0.2 mm from the surface of the active tip 27) was detected by a focusing transducer. A thermocouple with a core diameter of 0.3 mm was placed at position B (symmetric to position A), for temperature validation. A water tank 34 was placed on top of the tissue 33 to enhance the acoustics coupling.

A Nd:YAG laser with OPO (FIG. 2-210) was used for photoacoustic wave generation with a wavelength of 810 nm, a repetition frequency of 10 Hz, a pulse width of 6 ns, and output energy of ~6 mJ. The light beam from OPO (FIG. 2-210) was divided into two beams using a splitter mirror. One beam was received by a photodiode and displayed on an oscilloscope for calibration, while the other was delivered to the biological sample by Fiber 1 using a core diameter of 600 μm to generate the PA signal. The light beam of a diode laser 220 (wavelength 810 nm), power range 1~30 W, was delivered through Fiber 2 (FIG. 2) with a core diameter of 400 μm providing the photothermal effect. Several laser powers, 0.63, 0.93, and 1.24 W, were selected for thermal irradiation to demonstrate the photothermal effects. The two optical fibers were placed in parallel; light beams from two fibers were converged through a coupler to the same fiber (core diameter of 1000 μm) with the diffuse active tip.

The upper surface of the tissue sample 33 was coupled by plastic wrap to the water tank 37, reducing sound attenuation between different media. The depth-resolved photoacoustic signals from the sample 33 were collected by a focused ultrasound transducer 31, with a center frequency at 3.5 MHz. The signals were then transferred to an ultrasonic receiver 32 for amplitude filtering and amplification. Finally, the signals were displayed on a digital oscilloscope [FIG. 1-114-3]. In order to improve the signal-to-noise ratio, the signals on the digital oscilloscope [FIG. 1-114-3] were averaged 8 times and then saved for follow-up data processing. A step motor drove the electronic translation machine for 2-dimensional scanning and provided accurate control of the sample platform. The axial and lateral spatial resolutions of the PA imaging were 0.3 and 2 mm, respectively.

Referring now to FIG. 4, the temperatures measured by thermocouple and photoacoustic amplitudes were simultaneously recorded every 30 s during laser irradiation with different powers. FIG. 4 shows the temperature T, measured by the thermocouple at position B and PA signal measured by the transducer at position A (FIG. 3), as a function of thermal irradiation time t and laser power. The tissue temperature (shown in FIG.4a) and the PA signal (shown in Fig. 4b) increased sharply during the first 60 s and then slowly plateaued. The plateaued temperature increased with the power of the continuous-wave laser as shown in FIG. 4a.

Referring now to FIG. 5, the linear relationship between the PA signal at point A and the tissue temperature at point B (see FIG. 2) is presented. The straight line is a regression curve at 95% confidence ($r^2 > 0.94$ and p-value <0.01). The results in FIG. 5 are a graphical representation allowing a good regression of PA amplitude, p∝a·T+b in the range of 22 to 55° C., where a and b are 0.9 and 29.1, respectively. The symmetry around the active fiber tip ensures that the temperatures are the same at point A and point B (FIG. 3). Thus, we can use the temperature at point B, directly measured by thermocouple, for the temperature at point A for calibration of PA measurement.

Although the principle of the interstitial PA sensor for temperature measurement is the same as that in various previous studies, the uniqueness of this sensor is reflected on the synchronized interstitial PA temperature measurement and laser photothermal therapy. This coupled device allows real-time temperature measurement. Furthermore, an online analysis and control system using this sensor provides immediate feedback, so that treatment parameters can be adjusted during cancer treatment to achieve the desired thermal effect.

Referring now to FIG. 6, photoacoustic amplitude versus irradiation time is presented. To demonstrate the controlling capability of the unique sensor, the thermal radiation power of the laser was adjusted in an attempt to maintain the tissue temperature at a pre-determined level. The laser power for thermal irradiation was 1.24 W. The two dotted lines represent the PA amplitudes for the corresponding temperatures at 41 and 55° C., respectively, based on the linear relationship between PA signals and temperature (FIG. 3). When the highest tissue temperature reached 55° C., the 810-nm thermal laser was turned off, resulting in a temperature decrease. When the highest temperature decreased to 41° C., the thermal laser was turned on, and the temperature increased. The temperature could therefore be stabilized within the heat shock and cytotoxic range (41 to 55° C.), as shown by the results in FIG. 6. Tissue temperature can be similarly controlled within other ranges as well.

In this experiment, thermocouple and PA temperature measurement took place at the tissue boundary, close to the surface of the active fiber tip. The temperature distribution in the tissue away from the active fiber tip was simulated using the bioheat equation (Equation (4)). A two-dimensional temperature distribution is given in FIG. 7 (due to symmetry, only the lower half of the tissue configuration is shown), with the center of the active lens as the origin.

Referring now to FIG. 7, the two-dimensional temperature distribution in tissue is presented. The active diffusion tip is along the y direction, while the z direction is perpendicular to the active tip. FIG. 7a shows temperature distribution with a maximum temperature of 41° C. FIG. 7b shows temperature distribution with a maximum temperature of 55° C. with the black curve denoting a temperature of 41° C.

Laser Photothermal Therapy Using the Present Invention

Referring now to FIG. 8, the present invention [FIG. 1-10] may be used when performing laser photothermal therapy. The following steps may be incorporated into the procedures of the therapy:

1) Insert sterile laser fiber into sterile plastic sheath. In this step the pre-sterilized laser fiber is inserted into a loose plastic sterile outer sheath that allows laser fiber sterility to be better maintained during manipulation and insertion.

2) Insertion of flexible cannula/stylet assembly into tumor. At this step the cannula/stylet needle assembly [FIG. 1-119] is inserted sterilely through the skin and approximately 1.5 cm into the tumor. Placement of the cannula tip should be approximately 1.5 cm into the tumor as determined by palpation by the physician/operator.

3) Remove steel stylet (trocar or obturator rod) from Teflon cannula. At this step, the steel stylet which blocks the hollow Teflon cannula during insertion is withdrawn leaving the cannula in place and ready to receive the laser fiber.

4) Thread the laser fiber into the Teflon cannula. The laser fiber itself is inserted into the cannula all the way to the end of the cannula so that it is properly placed in the tumor. The aiming laser can be activated to monitor insertion and placement during the insertion if the tumor is superficial. It may be useful to lower the light levels in the room to make the aiming laser light more visible through the skin of the patient.

5) Test position of the laser fiber with aiming beam of laser. If the aiming beam has not been activated yet, it is useful to do so to check the placement of the laser fiber in the tumor.

6) Partial withdrawal of the Teflon cannula to expose laser fiber tip. In this step, the tip of the Teflon cannula is moved back to expose the optical fiber tip directly to the tumor tissue. This step is important to make sure that the cannula is not blocking the access of the laser energy to the target region of the tumor. If the cannula tip is not moved back to expose the fiber tip, it may end up melted to the laser fiber and/or interfere with energy transfer into the tissue.

7) Administration of laser energy. With the laser positioned and ready to treat, the desired infrared laser energy is delivered to the tumor center. Both the continuous-wave and the pulse lasers are activated at approximately the same time (simultaneous activation is not essential). The pulse laser light and continuous-wave laser light may be directed through two different fibers [FIG. 3] into the same active tip (e.g., 1-cm length and 1-mm diameter) in the target tissue through a fiber coupler.

8) Detection of photoacoustic signals and adjustment of laser power. The photoacoustic signals at position A [FIG. 3] may be detected through a transducer [FIG. 3-31] for temperature determination. Online analysis may be used to determine the tissue temperature distribution. The photoacoustic signal intensity is used to monitor the temperature changes in the target tissue and to guide the irradiation of the high-power laser to optimize the photothermal effect by adjusting the light intensity and irradiation time. Laser power may be adjusted automatically or manually) according to preset maximum and minimum temperatures.

9) Simultaneous withdrawal of the laser fiber & cannula. After laser treatment has been completed, the laser fiber and cannula are withdrawn simultaneously. If the laser fiber has been kinked slightly during insertion, the simultaneous withdrawal may limit further damage to the laser tip.

The invention claimed is:

1. A method of monitoring and optimizing laser photothermal tissue effect comprising:

providing a device adapted to monitor temperature changes in biological target tissue and control irradiation level and time duration of exposure to a high-power laser beam to optimize photothermal effect by adjusting light intensity and irradiation time period during laser photothermal therapy;

delivering through a first optical fiber a high-power continuous-wave laser beam from a laser with an optical parametric oscillator (OPO) to an active tip;

delivering through a second optical fiber a pulsed laser beam from a diode laser to said active tip;

dividing said high-power continuous-wave laser beam into a first beam and a second beam using a splitter mirror, and delivering said first beam to target tissue through said active tip and receiving said second beam by a photodiode and displaying a corresponding signal on an oscilloscope for calibration;

inducing photothermal effect to increase temperature in said target tissue using said continuous-wave laser beam, and producing a photoacoustic signal using said pulsed laser beam;

monitoring temperature changes in said target tissue using depth-resolved photoacoustic signals from the target tissue collected by a focused ultrasound transducer with a center frequency at approximately 3.5 MHz;

implementing an analysis and control system to provide immediate feedback for optimizing said photothermal effect by adjusting intensity and irradiation time of said high-power laser to maintain temperature in said target tissue corresponding to levels expressed in a temperature profile derived for biological material analogous to said target tissue.

2. The method according to claim 1, wherein said continuous-wave laser beam and said pulse laser beam are used to irradiate the same target tissue through an active tip approximately 1-cm in length and 1-mm in diameter positioned in said target tissue through a fiber coupler.

3. The method according to claim 1, wherein said continuous-wave laser beam and said pulse laser beam are delivered at the same time.

4. The method according to claim 1, wherein said temperature profile is determined using Pennes bioheat equation to describe the steady-state temperature fields of tissue irradiated by laser light using an interstitial diffuse fiber modeled as multiple isotropically radiating point sources distributed along a fiber tip with an interval of approximately 1 mm.

5. A system for monitoring and optimizing photothermal tissue effect during laser photothermal therapy, comprising:
a device adapted to monitor temperature changes in biological target tissue and control irradiation level and time duration of exposure to a high-power laser beam to optimize photothermal effect during laser photothermal therapy;
a first optical fiber for delivering a high-power continuous-wave laser beam from a laser with an optical parametric oscillator (OPO) to an active tip;
a second optical fiber for delivering a pulsed laser beam from a diode laser to said active tip;
a coupling for converging a high-power continuous-wave laser beam and a pulsed laser beam to an active tip to interstitially irradiate target tissue at the same time;
a continuous-wave laser configured with an optical parametric oscillator (OPO) adapted to produce a high-power laser beam for inducing photothermal effect to increase target tissue temperature;
a diode laser adapted to produce a pulsed laser beam creating a photoacoustic signal;
a splitter mirror adapted to divide said high-power continuous-wave laser bean from said OPO into a first beam and a second beam said first beam delivered to target tissue through said first optical fiber to said active tip and said second beam is received by a photodiode and a signal displayed on an oscilloscope for calibration;
a focused ultrasound transducer with a center frequency at approximately 3.5 MHz adapted to collect depth-resolved photoacoustic signals from said target tissue;
an online analysis and control system to provide immediate feedback for optimizing said photothermal effect by adjusting intensity and irradiation time of said high-power continuous-wave laser.

6. The system according to claim 5 wherein, said device contains a continuous-wave laser, a pulse laser, an optical fiber coupling component, a computer component, an acoustic coupling component, a scanning component connected to computer, a data acquisition card connected to an ultrasound energy exchanger, and to a computer network.

7. The system according to claim 6, wherein said device further comprises a sample-stabilizing component.

8. The system according to claim 5, wherein intensity and irradiation time of said high-power continuous-wave laser is adjusted to follow a temperature profile, and said temperature profile is determined using Pennes bioheat equation to describe the steady-state temperature fields of tissue irradiated by laser light using an interstitial diffuse fiber modeled as multiple isotropically radiating point sources distributed along a fiber tip with an interval of approximately 1 mm.

* * * * *

UNITED STATES PATENT AND TRADEMARK OFFICE
CERTIFICATE OF CORRECTION

| | |
|---|---|
| PATENT NO. | : 9,987,089 B2 |
| APPLICATION NO. | : 14/797430 |
| DATED | : June 5, 2018 |
| INVENTOR(S) | : Wei R. Chen et al. |

Page 1 of 1

It is certified that error appears in the above-identified patent and that said Letters Patent is hereby corrected as shown below:

In the Specification

At Column 1, please delete Lines 10-13 and insert in its place the following:
-- This invention was made with government support under R21 EB015509 awarded by the National Institutes of Health. The government has certain rights in the invention. --

Signed and Sealed this
Thirtieth Day of May, 2023

Katherine Kelly Vidal
*Director of the United States Patent and Trademark Office*